(12) United States Patent
Williams et al.

(10) Patent No.: US 7,815,692 B1
(45) Date of Patent: Oct. 19, 2010

(54) HAIR COLORING COMPOSITIONS

(75) Inventors: Barry W. Williams, Schamburg, IL (US); Glenn A. Shurney, Chicago, IL (US)

(73) Assignee: Universal Beauty Products, Inc., Elk Grove Village, IL (US)

( * ) Notice: Subject to any disclaimer, the term of this patent is extended or adjusted under 35 U.S.C. 154(b) by 0 days.

(21) Appl. No.: 12/512,947

(22) Filed: Jul. 30, 2009

(51) Int. Cl.
*A61Q 5/10* (2006.01)

(52) U.S. Cl. ................... 8/405; 8/426; 8/435; 8/463; 8/552; 8/555

(58) Field of Classification Search ............... 8/405, 8/426, 435, 463, 552, 555
See application file for complete search history.

(56) References Cited

U.S. PATENT DOCUMENTS

| | | | |
|---|---|---|---|
| 5,580,373 A | 12/1996 | Lane et al. | |
| 5,993,837 A | 11/1999 | Calello et al. | |
| 2006/0127337 A1 | 6/2006 | Radisson | |
| 2006/0127343 A1 | 6/2006 | Bernard et al. | |
| 2007/0014748 A1 | 1/2007 | Bernard et al. | |
| 2007/0065392 A1 | 3/2007 | Simonnet | |

FOREIGN PATENT DOCUMENTS

| | | |
|---|---|---|
| EP | 1201225 B1 | 5/2002 |
| WO | WO 2007137676 A2 | 12/2007 |

OTHER PUBLICATIONS

STIC Search Report dated Jun. 3, 2010.*
English abstract of the Patent KR 812118B1 (2006).*

* cited by examiner

*Primary Examiner*—Eisa B Elhilo
(74) *Attorney, Agent, or Firm*—Evan Law Group LLC

(57) ABSTRACT

A hair coloring composition comprises a N,N'-alkylurea, a hair dye, and a solvent.

17 Claims, No Drawings

HAIR COLORING COMPOSITIONS

BACKGROUND

Hair coloring compositions are used to color human hair. They are used for a variety of purposes; most commonly to return gray hair to its previous color, to change hair color to a shade regarded as more desirable, or to return hair to its original color after chemicals or environmental factors (e.g. tints, relaxers, sun bleaching) have discolored it.

Hair coloring compositions are typically categorized based on the length of time they effect the colored hair. The four most common classifications are "temporary," "semi-permanent," "demi-permanent," and "permanent."

The hair dye molecules in temporary hair colorings are large and, therefore, do not penetrate the cuticle layer, allowing only a coating action that may be removed by shampooing. Semi-permanent hair colorings usually include smaller hair dye molecules than those of temporary hair colorings, and are therefore able to penetrate the hair cuticle and reach the hair cortex.

Demi-permanent hair colorings usually last longer than the semi-permanent variety. The hair dye molecules in demi-permanent compositions enter the hair through the cuticle, as in the semi-permanent compositions, but once in the hair cortex they fuse with other molecules to give medium-sized color molecules. Because these molecules are larger in size, they now take much longer to wash out of the hair. Permanent hair coloring compositions are used for major hair color changes, for example going from black to blonde or vice-versa. When the hair dye molecules of permanent hair colorings enter the hair they react and expand to a size that cannot actually be washed out.

In order to increase the uptake of hair dye molecules into hair, hair coloring compositions may include a hair swelling agent. Without being bound to any particular theory, it is believed that the swelling agent increases hair swelling sufficiently to raise the cuticle of the hair shaft so that the color can be deposited therein.

Conventional swelling agents include, for example, ammonia, urea, thiourea, acetic acid, phosphoric acid, formic acid, formamide, ethyl amine, alkali halides such as potassium iodide, sodium bromide, lithium bromide, and lithium chloride. Ammonia is the most commonly used swelling agent. Unfortunately, conventional swelling agents are often characterized by an unpleasant odor and/or can be harsh and damaging to hair. This is especially true if the hair is dyed on a frequent basis.

SUMMARY

In a first aspect, the invention provides hair coloring compositions comprising an N,N'-alkylurea, a hair dye, and a solvent.

In a second aspect, the invention provides methods for coloring hair comprising contacting hair with a composition comprising an N,N'-alkylurea, a hair dye, and a solvent.

In a third aspect, the invention provides improved hair coloring compositions comprising a hair dye and a solvent, with the improvement of replacing the swelling agent with an N,N'-alkylurea.

In a fourth aspect, the invention provides improved hair coloring compositions comprising a hair dye and a solvent, with the improvement of replacing the ammonia with an N,N'-alkylurea.

In a fifth aspect, the invention provides hair coloring compositions produced by a process comprising mixing ingredients comprising an N,N'-alkylurea, a hair dye, and a solvent.

DEFINITIONS

The following definitions are included to provide a clear and consistent understanding of the specification and claims.

The term "(w/w)" is defined as the ratio of the weight of a component to the weight of the composition containing the component.

The term "cPs" is defined as centipoise.

The term "aminoalcohol" is defined as a compound containing an amine moiety and an alcohol moiety.

DETAILED DESCRIPTION

The present invention makes use of the discovery that hair coloring compositions containing N,N'-alkylureas provide for better and more stable coloring than compositions containing conventional swelling agents. Furthermore, compositions containing N,N'-alkylureas are milder on the hair and are characterized by a better odor than conventional hair coloring formulations.

The hair coloring composition of the invention includes an N,N'-alkylurea. An "N,N'-alkylurea" is defined as a compound of Formula I or salts thereof:

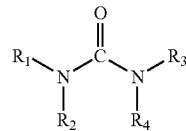

Formula 1

At least one of moieties $R_1$ and $R_2$ and at least one of moieties $R_3$ and $R_4$ are alkyl groups independently containing 1 to 10 carbon atoms. The alkyl groups may be linear, branched, or cyclic moieties, optionally containing one or more heteroatoms selected from O, N, and S. Two or more of $R_1$, $R_2$, $R_3$, and $R_4$ may be part of the same cyclic or heterocyclic moiety. Optionally, one or more of the alkyl groups may be independently substituted with one or more moieties, such as —OH, —NH$_2$, —SH, halogen, —NO$_2$, —OPO$_3$H$_2$, —PO$_3$H$_2$, —C(O)CH$_3$, and —CN.

Three or all of $R_1$, $R_2$, $R_3$, and $R_4$ may optionally be alkyl groups. Particularly preferred are N,N'-dimethyl urea, N,N'-dimethylpropylene urea (DMPU), and N,N'-tetrabutyl urea (TBU).

The hair coloring composition preferably includes 0.01% (w/w) to 15% (w/w) of an N,N'-alkylurea. More preferably, the amount of N,N'-alkylurea in the composition is from 0.1% (w/w) to 5% (w/w), most preferably 0.3% (w/w) to 2% (w/w).

The composition also includes a hair dye. The hair dye is preferably semi-permanent, demi-permanent or permanent, but the present invention is particularly suitable for use with semi-permanent dyes. Example hair dyes include those designated as "hair dyes and colors" by the International Nomenclature for Cosmetic Ingredients (INCI) (see International Cosmetic Ingredient Dictionary and Handbook, Twelfth Edition, 2008, pages 3403-3406).

Common classes of hair dyes include metal salts, such as lead acetate or bismuth citrate, and synthetic organic dyes, for example polyunsaturated, aromatic and polyaromatic compounds. Preferred hair dyes include those available under the brand names of ARIANOR®, COVACAP®, COVARIANE®, and COVASTYLE® (all by Sensient Cosmetic Technologies/LCW, South Plainfield, N.J.). Particularly preferred hair dyes are listed below in Table 1:

TABLE 1

| INCI Name | Technical Name(s) | Trade Name(s) |
|---|---|---|
| Basic Blue 99 | 3-[(4-Amino-6-Bromo-5,8-Dihydro-1-Hydroxy-8-Imino-5-Oxo-2-Naphthalenyl)Amino]-N,N,N-Trimethyl-benzenaminium Chloride Benzenaminium, 3-[(4-Amino-6-Bromo-5,8-Dihydro-1-Hydroxy-8-Imino-5-Oxo-2-Naphthalenyl)Amino]-N,N,N-Trimethyl-Chloride | Arianor Steel Blue 306004 Jarocol Steel Blue |
| Basic Brown 16 | [8-[(p-Aminophenyl)Azo]-7-Hydroxy-2-Naphthyl]Trimethylammonium Chloride Ammonium, [8-[(p-Aminophenyl)Azo]-7-Hydroxy-2-Naphthyl]Trimethyl-, Chloride | Arianor Mahogany 306002 Jarocol Mahogany |
| Basic Brown 17 | [8-[(4-Amino-3-Nitrophenyl)Azo]-7-Hydroxy-2-Naphthyl]Trimethylammonium Chloride [8-[(4-Amino-3-Nitrophenyl)Azo]-7-Hydroxy-N,N,N-Trimethyl-2-Napthalenaminium Chloride 2-Napthalenaminium, [8-[(4-Amino-3-Nitrophenyl)Azo]-7-Hydroxy-N,N,N-Trimethyl-, Chloride | Arianor Sienna Brown 306001 Jarocol Sienna Brown |
| Basic Red 76 | 7-Hydroxy-8-[(2-Methoxyphenyl)Azo]-N,N,N-Trimethyl-2-Naphthalenaminium Chloride 2-Naphthalenaminium, 7-Hydroxy-8-[(2-Methoxyphenyl)Azo]-N,N,N-Trimethyl-, Chloride | Arianor Madder Red 306003 Jarocol Madder Red |
| Basic Red 118 | [8-[(4-Amino-2-Nitrophenyl)azo]-7-Hydroxy-2-Naphthyl]trimethylammonium Chloride | Arianor Bordeaux 306006 |
| Basic Yellow 57 | Benzenaminium, 3-[(4,5-Dihydro-3-Methyl-5-Oxo-1-Phenyl-1H-Pyrazol-4-yl)Azo]-N,N,N-Trimethyl-, Chloride 3-[(4,5-Dihydro-3-Methyl-5-Oxo-1-Phenyl-1H-Pyrazol-4-yl)Azo]-N,N,N-Trimethylbenzenaminium Chloride | Arianor Straw Yellow 306005 Jarocol Straw Yellow |
| Acid Blue 9 | Benzenemethanaminium, N-Ethyl-N-[4-[[4-Ethyl[(3-Sulfophenyl)Methyl]Amino]Phenyl](2-Sulfophenyl)Methylene-2,5-Cyclohexadien-1-ylidene]-3-Sulfo, Hydroxide, Inner Salt, Disodium Salt N-Ethyl-N-[4-[[4-[Ethyl[(3-Sulfophenyl)Methyl]Amino]Phenyl](2-Sulfophenyl)Methylene]-2,5-Cyclohexadien-1-ylidene]-3-Sulfobenzenemethanaminium Hydroxide, Inner Salt, Disodium Salt | Covacap Bleu W 6102 |
| Acid Yellow 23 | 4,5-Dihydro-5-Oxo-1-(4-Sulfophenyl)-4-[(4-Sulfophenyl)Azo]-1H-Pyrazole-3-Carboxylic Acid, Trisodium Salt 1H-Pyrazole-3-Carboxylic Acid, 4,5-Dihydro-5-Oxo-1-(4-Sulfophenyl)-4-[(4-Sulfophenyl)Azo]-, Trisodium Salt | Covacap Jaune W 1100 |
| Acid Yellow 3 | 1,3-Isobenzofurandione, Reaction Products with Methyiquinoline and Quinoline, Sulfonated | Covacap Jaune W 1104 |
| Acid Black 1 | 4-Amino-5-Hydroxy-3-[(4-Nitrophenyl)Azo]-6-(Phenylazo)-2,7-Naphthalenedisulfonic Acid, Disodium Salt 2,7-Naphthalenedisulfonic Acid, 4-Amino-5-Hydroxy-3-[(4-Nitrophenyl)Azo]-6-(Phenylazo)-, Disodium Salt | Covacap Noir W 9109 |

TABLE 1-continued

| INCI Name | Technical Name(s) | Trade Name(s) |
|---|---|---|
| Acid Orange 7 | Benzenesulfonic Acid, 4-[(2-Hydroxy-1-Naphthalenyl)Azo]-, Monosodium Salt<br>4-[(2-Hydroxy-1-Naphthalenyl)Azo]Benzenesulfonic Acid, Monosodium Salt | Covacap Orange W 2100 |
| Acid Violet 43 | Benzenesulfonic Acid, 2-[(9,10-Dihydro-4-Hydroxy-9,10-Dioxo-1-Anthracenyl)Amino]-5-Methyl-, Monosodium Salt<br>2-[(9,10-Dihydro-4-Hydroxy-9,10-Dioxo-1-Anthracenyl)Amino]-5-Methylbenzenesulfonic Acid, Monosodium Salt<br>m-Toluenesulfonic Acid, 6-((4-Hydroxy-1-anthraquinonyl)amino)-Sodium Salt | Covacap Pourpre W 5102 Conc 120<br>Jarocol Violet 43 |
| Acid Red 52 | N-[6-(Diethylamino)-9-(2,4-Disulfophenyl)-3H-Xanthen-3-ylidene]-N-Ethyl Ethanaminium, Hydroxide, Inner Salt, Sodium Salt<br>Ethanaminium, N-[6-(Diethylamino)-9-(2,4-Disulfophenyl)-3H-Xanthen-3-ylidene]-N-Ethyl-, Hydroxide, Inner Salt, Sodium Salt<br>Xanthylium, 3,6-Bis(Diethylamino)-9-(2,4-Disulfophenyl)-, Hydroxide, Inner Salt, Sodium Salt | Covacap Rose W 4102 |
| Acid Red 18 | 7-Hydroxy-8-[(4-Sulfo-1-Naphthalenyl)Azo]-1,3-Naphthalenedisulfonic Acid, Trisodium Salt<br>1,3-Naphthalenedisulfonic Acid, 7-Hydroxy-8-[(4-Sulfo-1-Naphthalenyl)Azo]-, Trisodium Salt | Covacap Rouge W 3102 |
| Acid Red 33 | 5-Amino-4-Hydroxy-3-(Phenylazo)-2,7-Naphthalenedisulfonic Acid, Disodium Salt<br>2,7-Naphthalenedisulfonic Acid, 5-Amino-4-Hydroxy-3-(Phenylazo)-, Disodium Salt | Covacap Rouge W 3103 |
| Acid Red 14 | 4-Hydroxy-3-[(4-Sulfo-1-Naphthalenyl)Azo]-1-Naphthalenesulfonic Acid, Disodium Salt<br>1-Naphthalenesulfonic Acid, 4-Hydroxy-3-[(4-Sulfo-1-Naphthalenyl)Azo]-, Disodium Salt | Covacap Rouge W 3104 |
| Acid Green 25 | Benzenesulfonic Acid, 2,2'-[(9,10-Dihydro-9,10-Dioxo-1,4-Anthracenediyl)Diimino]Bis(5-Methyl)-, Disodium Salt<br>2,2'-[(9,10-Dihydro-9,10-Dioxo-1,4-Anthracenediyl)Diimino]Bis(5-Methyl)Benzenesulfonic Acid, Disodium Salt<br>m-Toluenesulfonic Acid, 6,6'-(1,4-Anthraquinonylenediimino)di-, Disodium Salt | Covacap Vert W 7103 |
| HC Blue No. 2 | Ethanol, 2,2'-[[4-[(2-Hydroxyethyl)Amino]-3-Nitrophenyl]Imino]Bis-<br>2,2'-[[4-[(2-Hydroxyethyl)Amino]-3-Nitrophenyl]Imino]Bisethanol<br>N1,N4,N4-Tris(2-Hydroxyethyl)-2-Nitro-p-Phenylenediamine | Covariane Bleu W 6122<br>Jarocol Blue 2 |
| Basic Blue 26 | N-[4-[[4-(Dimethylamino)Phenyl][4-(Phenylamino)-1-Naphthalenyl]Methylene]-2,5-Cyclohexadien-1-ylidene]-N-Methyl-2-Methanaminium Chloride<br>2-Methanaminium, N-[4-[[4-(Dimethylamino)-Phenyl][4-(Phenylamino)-1-Naphthalenyl]Methylene]-2,5- | Covariane Bleu W 6126 |

TABLE 1-continued

| INCI Name | Technical Name(s) | Trade Name(s) |
|---|---|---|
| | Cyclohexadien-1-ylidene]-N-Methyl-, Chloride | |
| HC Yellow No. 2 | Ethanol, 2-(o-nitroanilino)- Ethanol, 2-[(2-Nitrophenyl)Amino- N-(2-Hydroxyethyl)-2-Nitroaniline 2-[(2-Nitrophenyl)Amino]Ethanol | Covariane Jaune W 1122 Jarocol Yellow 2 |
| HC Yellow No. 5 | 2-[(2-Amino-4-Nitrophenyl)Amino]Ethanol Ethanol, 2-(2-amino-4-nitroanilino)- Ethanol, 2-[(2-Amino-4- Nitrophenyl)Amino]- N1-(2-Hydroxyethyl)-4-Nitro-o- Phenylenediamine | Covariane Jaune W 1125 Jarocol Yellow 5 |
| 4-Amino-3-Nitrophenol | 2-Amino-5-Hydroxynitrobenzene 3-Nitro-4-Aminophenol 2-Nitro-4-Hydroxyaniline Phenol, 4-Amino-3-Nitro- | Covariane Orange W 2121 Jarocol 4A3NP |
| N,N'-Bis(2-Hydroxyethyl)- 2-Nitro-p- Phenylenediamine | Ethanol, 2,2'-[(2-Nitro-1,4- Phenylene)Diimino]Bis- 2,2'-[(2-Nitro-1,4- Phenylene)Diimino]Bisethanol | Covariane Pourpre W 5121 Jarocol Violet 14D |
| HC Red No. 3 | 2-[(4-Amino-2-Nitrophenyl)Amino]Ethanol Ethanol, 2-((4-amino-2- nitrophenyl)amino)4-(2- Hydroxyethyl)amino-3-nitroaniline N1-(2-Hydroxyethyl)-2-Nitro-p- Phenylenediamine | Covariane Rouge W 3123 Jarocol Red 3 |
| 4-Hydroxypropylamino-3- Nitrophenol | 4-Hydroxypropylamino-2-Nitrophenol 4-(3-Hydroxypropylamino)-3- Nitrophenol Phenol, 4-[(3-Hydroxypropyl)amino]- 3-Nitro- | Covariane Rouge W 3127 |
| 2-Amino-4- Hydroxyethylaminoanisole Sulfate | 2-Amino-4-[(2- Hydroxyethyl)Amino]Anisole Sulfate 2-[(3-Amino-4- Methoxyphenyl)Amino]Ethanol Sulfate Ethanol, 2-[(3-Amino-4- Methoxyphenyl)Amino]-, Sulfate | Covastyle AHEAS Jarocol AHEA |
| 4-Amino-2- Hydroxytoluene | 5-Amino-o-Cresol p-Amino-o-cresol 4-Amino-2-Hydroxy-1- Methylbenzene 5-Amino-2-Methylphenol Phenol, 5-Amino-2-Methyl- | Covastyle AHT Jarocol 2M5AP |
| 4-Chlororesorcinol | 1,3-Benzenediol, 4-Chloro- 4-Chloro-1,3-Benzenediol p-Chlororesorcinol 2,4-Dihydroxychlorobenzene | Covastyle 4 CLR |
| m-Aminophenol | 3-Aminophenol m-Hydroxyaminobenzene 3-Hydroxyaniline 3-Hydroxybenzenamine m-Hydroxyphenylamine Phenol, 3-Amino- | Covastyle MAP Jarocol MAP |
| m-Phenylenediamine | m-Aminoaniline 1,3-Benzenediamine 1,3-Diaminobenzene 1,3-Phenylenediamine | Covastyle MPD |
| m-Phenylenediamine Sulfate | 1,3-Benzenediamine, Sulfate 1,3-Phenylenediamine Sulfate m-Xylenediamine Sulfate | Covastyle MPDS |
| 2-Nitro-p- Phenylenediamine | 4-Amino-2-nitroaniline 1,4-Benzenediamine, 2-Nitro- 2,5-Diaminonitrobenzene 2-Nitro-1,4-Diaminobenzene o-Nitro-p-Phenylenediamine | Covastyle 2NPPD Jarocol 2NPPD |
| p-Aminophenol | 4-Amino-1-Hydroxybenzene 4-Aminophenol 4-Hydroxyaniline 4-Hydroxybenzenamine 4-Hydroxyphenylamine Phenol, 4-Amino- Phenol, p-Amino | Covastyle PAP Jarocol PAP |

TABLE 1-continued

| INCI Name | Technical Name(s) | Trade Name(s) |
|---|---|---|
| p-Phenylenediamine | p-Aminoaniline<br>1,4-Benzenediamine<br>p-Diaminobenzene<br>1,4-Phenylenediamine | Covastyle<br>PPD<br>Jarocol PPD |
| p-Phenylenediamine Sulfate | 1,4-Benzenediamine, Sulfate<br>1,4-Benzenediamine Sulfate (1:1) | Covastyle PPDS<br>Jarocol PPDS |
| Resorcinol | 1,3-Benzenediol<br>m-Dihydroxybenzene<br>m-Hydroquinone<br>3-Hydroxyphenol<br>m-Phenylenediol | Covastyle RCN<br>Jaracol RL |

The amount of hair dye may be varied according to the desired hue and intensity of color. Preferably, the composition includes 0.001% (w/w) to 5% (w/w) of a hair dye. More preferably, the amount of hair dye in the composition is from 0.01% (w/w) to 2.5% (w/w), most preferably 0.1% (w/w) to 1.5% (w/w).

The composition includes a solvent, preferably water and/or an alcohol. Preferred alcohols include methanol, ethanol, propanol, isopropanol, butanol, sec-butanol, isobutanol, tert-butanol, 1-pentanol, 2-pentanol, 3-pentanol, 3-methyl-1-butanol, 2-methyl-1-butanol, 2,2-dimethyl-1-propanol, 3-methyl-2-butanol, and 2-methyl-2-butanol. Ethanol is an especially preferred alcohol.

The composition may be in the form of a solution, a suspension, a colloid, a dispersion, a slurry, a gel, a mousse, a cream, a shampoo, or a hair conditioner. The composition may also include one or more additional ingredients.

For instance, a co-solvent may be included in the composition to increase the solubility of other ingredients. Example co-solvents include propylene glycol, glycerin, and glycol ethers. Preferred glycol ethers include 2-methoxyethanol, 2-ethoxyethanol, 2-propoxyethanol, 2-isopropoxyethanol, 2-butoxyethanol, 2-phenoxyethanol, 2-benzyloxyethanol, 2(2-methoxyethoxy)ethanol, 2(2-ethoxyethoxy)ethanol, and 2-(butoxyethoxy)ethanol. Particularly preferred co-solvents include propylene glycol and 2(2-ethoxyethoxy)ethanol, which is available commercially, for example, as TRANSCUTOL® CG (Gattefossé, Paramus, N.J.).

The viscosity of the composition is preferably 500 cPs to 12,000 cPs. More preferably, the viscosity is 3,000 cPS to 6,000 cPs, most preferably 3,500 cPs to 5,000 cPs. A thickener may be added to attain the desired viscosity. Thickeners used in cosmetics, such as polyethylene glycol (PEG), polyacrylic acid, and vegetable gum, are preferred. Cellulose-derived thickeners, for example hydroxymethylcellulose, hydroxyethylcellulose, and hydroxypropylcellulose, are particularly preferred. Most preferred is hydroxyethylcellulose, commercially available, for example, as NATROSOL® (Aqualon North America, Wilmington, Del.). The composition preferably includes 0.05% (w/w) to 5% (w/w) of thickener. The amount of thickener is more preferably 0.1% (w/w) to 2% (w/w), most preferably 0.5% (w/w) to 1.2% (w/w).

More intense and longer lasting hair color may be obtained by adding a fixative to the composition. Examples include those designated as "quaternium" and "polyquaternium" by the INCI. Suitable fixatives include cationic, anionic, and amphoteric polymers. Examples include polymers prepared by polymerizing a quaternary ammonium monomer such as dimethyl diallyl ammonium chloride (DMDAAC). Preferred fixatives are those prepared by polymerizing a quaternary ammonium diallyl dialkyl ammonium monomer and an anionic monomer such as acrylic acid or methacrylic acid, for instance the polymers disclosed in U.S. Pat. No. 4,772,462. Particularly preferred polymers are those available under the brand name of MERQUAT® (Nalco, Naperville, Ill.). Most preferred is acrylic acid-diallyldimethylammonium chloride polymer, designated in the INCI dictionary as Polyquaternium-22 and commercially available as MERQUAT® 295.

Suitable fixatives also include silicone compounds having at least a quaternary ammonium moiety, such as for example cationic organosiloxanes having the general structural formula (IV), depicted in columns 7 and 8 of U.S. Pat. No. 5,328,685:

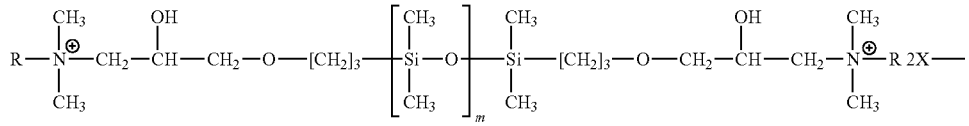

(IV)

Wherein R is an alkyl group having one to about 22 carbon atoms, m is from about 5 to about 50, and X is a water-soluble anion.

A specific example of a silicone compound having general structural formula (IV) is designated in the INCI dictionary as Quaternium-80. Commercially available preparations of Quaternium-80 include COVAFIX® 123 (Sensient Cosmetic Technologies/LCW, South Plainfield, N.J.), a solution of Quaternium-80 in propylene glycol and benzylalcohol.

The composition preferably includes 0.5% (w/w) to 20% (w/w) of a fixative. The amount of fixative is more preferably 1% (w/w) to 6% (w/w), most preferably 2% (w/w) to 4% (w/w).

The pH of the composition is preferably 7.0 to 9.0. More preferably, the pH is 7.1 to 8.5, most preferably 7.3 to 8.3. A pH adjusting agent, for example an acid, base, or buffer, may be added to the composition to adjust the pH to desired values. Example pH adjusting agents include organic acids, mineral acids, ammonia, amines, and alkali metal and alkaline earth metal salts of anions such as hydroxide, carbonate, acetate, carbamate, citrate, glutamate, phosphate, polyphosphate, silicate, and borate.

Aminoalcohols are preferred pH adjusting agents. Example aminoalcohols include monoethanolamine, monopropanolamine, diethanolamine, dipropanolamine, triethanolamine, 2-amino-2-methyl-propanol, 2-amino-2-ethyl-1,3-propanediol, 2-dimethylamino-2-methylpropanol (DMAMP), tris(hydroxymethyl)amino methane (TRIS), 1,3-diamino-propanol (DAP), N,N'-tetra-methyl-1,3-diamino-2-propanol, and N-methyl diethanolamine (MDEA). Triethanolamine is especially preferred.

Preservatives, preferably chosen from those that do not interfere with the dye of the composition, may be added to the composition. Example preservatives include the parabens, such as methylparaben, ethylparaben, propylparaben, butylparaben, and their salts. Other preservatives include 1,3-bis(hydroxymethyl)-5,5-dimethylimidazolidine-2,4-dione (also known as DMDM hydantoin), benzoic acid, and sodium hydroxymethyl glycinate, which is commercially available, for example, as MACKSTAT® SHG (McIntyre Group, University Park, Ill.). The composition preferably includes 0.01% (w/w) to 1% (w/w) of a preservative. The amount of preservative is more preferably 0.1% (w/w) to 0.9% (w/w), most preferably 0.2% (w/w) to 0.8% (w/w).

Chelating agents may also be part of the composition, for example to prevent oxidation reactions catalyzed by metal ions. Example chelating agents include ethylenediaminetetraacetic acid (EDTA), ethylene glycol tetraacetic acid (EGTA), N,N'-ethylenediaminediacetic acid ($H_2$EDDA), 1,2-diaminocyclohexane-N,N,N',N'-tetraacetic acid ($H_4$CyDTA), 2,3-dimercapto-1-propanesulfonic acid (DMPS), dimercaptosuccinic acid (DMSA), diethylene triamine pentaacetic acid (DTPA), and crown ethers, as well as salts and complexes thereof.

The composition preferably includes 0.01% (w/w) to 1% (w/w) of a chelating agent. The amount of chelating agent is more preferably 0.1% (w/w) to 0.9% (w/w), most preferably 0.2% (w/w) to 0.8% (w/w).

Perfumes may also be added to the composition, either to mask or enhance its fragrance.

Instructions may be optionally provided with the hair coloring composition of the invention. Instructions may include directions regarding how to apply the composition to hair. The instructions may be present in a variety of forms, including one or more printed sheets, printing on the outside or inside the exterior package, writing incorporated on one or more of the containers enclosed in the exterior package, a CD-ROM, a DVD-ROM, a uniform resource locator (URL) for a website, and the like.

The optional exterior package may be sized and configured to contain one or more other components of the composition. An exterior package may be a cup, a bottle, a vial, a tube, or the like, which may be formed in part or in whole from plastic, glass, paper, STYROFOAM®, and the like.

The optional exterior package may include one or more supporting structures, such as walls, wells, movable or removable trays, etc., so as to segregate the various components of the composition. Supporting structures may be formed in part or in whole from plastic, glass, paper, STYROFOAM®, and the like.

The following examples are provided to illustrate one or more preferred hair coloring compositions of the invention. Numerous variations may be made to the following examples that lie within the scope of the invention.

EXAMPLES

Example 1

Specific gravity: 1

| Ingredient | % w/w |
|---|---|
| Deionized water | 83.44% |
| NATROSOL ® 250HHR CS | 0.80% |
| Methylparaben | 0.20% |
| Hair Dyes | 1.11% |
| Propylene Glycol | 5.00% |
| MERQUAT ® 295 | 2.00% |
| N,N'-dimethyl urea | 0.50% |
| COVAFIX ® 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.30% |
| Total | 100.00% |

Example 2

Specific gravity: 1

| Ingredient | % w/w |
|---|---|
| Deionized water | 83.39% |
| NATROSOL ® 250HHR CS | 0.80% |
| Methylparaben | 0.20% |
| Hair Dyes | 1.16% |
| Propylene Glycol | 5.00% |
| MERQUAT ® 295 | 2.00% |
| Dimethyl UREA | 0.50% |
| Covafix 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.30% |
| Total | 100.00% |

Example 3

Specific gravity: 1

| Ingredient | % w/w |
|---|---|
| Deionized water | 83.46% |
| NATROSOL ® 250HHR CS | 0.80% |
| Methylparaben | 0.20% |
| Hair Dyes | 1.1% |
| Propylene Glycol | 5.00% |
| MERQUAT ® 295 | 2.00% |
| Dimethyl UREA | 0.50% |
| COVAFIX ® 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.30% |
| Total | 100.00% |

Example 4

Specific gravity: 1

| Ingredient | % w/w |
|---|---|
| Deionized water | 84.10% |
| NATROSOL ® 250HHR CS | 0.80% |
| Methylparaben | 0.20% |
| Hair Dyes | 0.55% |
| Propylene Glycol | 5.00% |
| MERQUAT ® 295 | 2.00% |
| Dimethyl UREA | 0.50% |
| COVAFIX ® 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.20% |
| Total | 100.00% |

Example 5

Specific gravity: 1

| Description | % w/w |
|---|---|
| Deionized water | 83.75% |
| NATRASOL ® 250 HHR CS | 0.80% |
| Methylparaben | 0.20% |
| Hair Dyes | 0.78% |
| Propylene Glycol | 5.00% |
| MERQUAT ® 295 | 2.00% |
| Dimethyl UREA | 0.50% |
| TRANSCUTOL ® CG | 3.00% |
| COVAFIX ® 123 | 3.00% |
| EDTA (powder) | 0.20% |
| DMDM Hydantoin | 0.25% |
| Tropical Escape Perfume | 0.20% |
| TEA 85% | 0.35% |
| Total | 100% |

Example 6

Specific gravity: 1

| Ingredient | % w/w |
|---|---|
| Deionized water | 84.35% |
| NATROSOL ® 250HHR CS | 0.80% |
| Methylparaben | 0.20% |
| Hair Dyes | 0.3% |
| Propylene Glycol | 5.00% |
| MERQUAT ® 295 | 2.00% |
| Dimethyl UREA | 0.50% |
| Covafix 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.20% |
| Total | 100.00% |

Example 7

Specific gravity: 1

| Ingredient | % w/w |
|---|---|
| Deionized water | 84.05% |
| NATROSOL ® 250HHR CS | 0.80% |

Example 7-continued

Specific gravity: 1

| Ingredient | % w/w |
|---|---|
| Methylparaben | 0.20% |
| Hair Dyes | 0.45% |
| Propylene Glycol | 5.00% |
| MERQUAT ® 295 | 2.00% |
| Dimethyl UREA | 0.50% |
| COVAFIX ® 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.20% |
| Total | 99.85% |

Example 8

Specific gravity: 1

| Ingredient | % w/w |
|---|---|
| Deionized water | 84.05% |
| NATROSOL ® 250HHR CS | 0.80% |
| Methylparaben | 0.20% |
| Hair Dyes | 0.6% |
| Propylene Glycol | 5.00% |
| MERQUAT ® 295 | 2.00% |
| Dimethyl UREA | 0.50% |
| COVAFIX ® 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.20% |
| Total | 100.00% |

Example 9

Specific gravity: 1

| Ingredient | % w/w |
|---|---|
| Deionized water | 84.07% |
| NATROSOL ® 250HHR CS | 0.80% |
| Methylparaben | 0.20% |
| Hair Dyes | 0.58% |
| Propylene Glycol | 5.00% |
| MERQUAT ® 295 | 2.00% |
| Dimethyl UREA | 0.50% |
| COVAFIX ® 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.20% |
| Total | 100.00% |

Example 10

Specific gravity: 1

| Ingredient | % w/w |
|---|---|
| Deionized water | 83.62% |
| NATROSOL ® 250HHR CS | 0.80% |
| Methylparaben | 0.20% |
| Hair Dyes | 1.03% |

Example 10-continued

Specific gravity: 1

| Ingredient | % w/w |
|---|---|
| Propylene Glycol | 5.00% |
| MERQUAT ® 295 | 2.00% |
| Dimethyl UREA | 0.50% |
| COVAFIX ® 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.20% |
| Total | 100.00% |

Example 11

Specific gravity: 1

| Ingredient | % w/w |
|---|---|
| Deionized water | 83.57% |
| NATROSOL ® 250HHR CS | 0.80% |
| Methylparaben | 0.20% |
| Hair Dye | 1.03% |
| Propylene Glycol | 5.00% |
| MERQUAT ® 295 | 2.00% |
| Dimethyl UREA | 0.50% |
| TRANSCUTOL ® CG | 3.00% |
| COVAFIX ® 123 | 3.00% |
| EDTA (powder) | 0.25% |
| DMDM Hydantoin | 0.20% |
| TEA | 0.25% |
| Tropical Escape Perfume | 0.20% |
| Total | 100.00% |

Example 12

Specific gravity: 1

| Ingredient | % w/w |
|---|---|
| Deionized water | 83.70% |
| NATROSOL ® 250HHR CS | 0.80% |
| Methylparaben | 0.20% |
| Hair Dyes | 0.95% |
| Propylene Glycol | 5.00% |
| MERQUAT ® 295 | 2.00% |
| Dimethyl UREA | 0.50% |
| COVAFIX ® 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.20% |
| Total | 100.00% |

Example 13

Specific gravity: 1

| Ingredient | % w/w |
|---|---|
| Deionized water | 84.63% |
| NATROSOL ® 250HHR CS | 0.80% |
| Methylparaben | 0.20% |
| Hair Dye | 0.02% |
| Propylene Glycol | 5.00% |
| MERQUAT ® 295 | 2.00% |

Example 13-continued

Specific gravity: 1

| Ingredient | % w/w |
|---|---|
| Dimethyl urea | 0.50% |
| COVAFIX ® 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.20% |
| Total | 100.00% |

Example 14

Specific gravity: 1

| Ingredient | % w/w |
|---|---|
| Deionized water | 84.65% |
| NATROSOL ® 250HHR CS | 0.80% |
| Methylparaben | 0.20% |
| Propylene Glycol | 5.00% |
| MERQUAT ® 295 | 2.00% |
| Dimethyl urea | 0.50% |
| COVAFIX ® 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.20% |
| Total | 100.00% |

Example 15

Specific gravity: 1

| Description | % w/w |
|---|---|
| Deionized water | 84.12% |
| NATROSOL ® 250HHR CS | 0.90% |
| Methylparaben | 0.20% |
| Hair Dyes | 0.43% |
| Propylene Glycol | 5.00% |
| MERQUAT ® 295 | 2.00% |
| Dimethyl urea | 0.50% |
| COVAFIX ® 123 | 3.00% |
| TRANSCUTOL ® CG | 3.00% |
| EDTA (powder) | 0.25% |
| DMDM Hydantoin | 0.20% |
| Tropical Escape perfume | 0.20% |
| TEA 99% | 0.20% |
| Total | 100.00% |

Example 16

Specific gravity: 1

| Description | % w/w |
|---|---|
| Deionized water | 83.63% |
| NATROSOL ® 250HHR CS | 0.90% |
| Methylparaben | 0.20% |
| Hair Dyes | 0.92% |
| Propylene Glycol | 5.00% |
| MERQUAT ® 295 | 2.00% |
| Dimethyl urea | 0.50% |
| COVAFIX ® 123 | 3.00% |
| TRANSCUTOL ® CG | 3.00% |

Example 16-continued

Specific gravity: 1

| Description | % w/w |
|---|---|
| EDTA (powder) | 0.25% |
| DMDM Hydantoin | 0.20% |
| Tropical Escape Perfume | 0.20% |
| TEA 99% | 0.20% |
| Total | 100.00% |

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A hair coloring composition, comprising:
    an N,N'-alkylurea selected from the group consisting of N,N'-dimethyl urea, N,N'-dimethylpropylene urea, N,N'-tetrabutyl urea and mixtures thereof,
    a hair dye, acrylic acid diallyldimethylammonium chloride polymer and
    a solvent.

2. The composition of claim 1, wherein the N,N'-alkylurea is N,N'-dimethyl urea.

3. The composition of claim 1, wherein the composition comprises 0.01% (w/w) to 15% (w/w) of the N,N'-alkylurea.

4. The composition of claim 1, wherein the composition comprises 0.1% (w/w) to 5% (w/w) of the N,N'-alkylurea.

5. The composition of claim 1, wherein the composition comprises 0.3% (w/w) to 2% (w/w) of the N,N'-alkylurea.

6. The composition of claim 1, wherein the hair dye is selected from the group consisting of Basic Blue 99, Basic Brown 16, Basic Brown 17, Basic Red 76, Basic Red 118, Basic Yellow 57, Acid Blue 9, Acid Yellow 23, Acid Yellow 3, Acid Black 1, Acid Orange 7, Acid Violet 43, Acid Red 52, Acid Red 18, Acid Red 33, Acid Red 14, Acid Green 25, HC Blue Number 2, Basic Blue 26, HC Yellow Number 2, HC Yellow Number 5,4-Amino-3-Nitrophenol, N,N'-Bis(2-Hydroxyethyl)-2-Nitro-p-Phenylenediamine, HC Red Number 3,4-Hydroxypropylamino-3-Nitrophenol, 2-Amino-4-Hydroxyethylaminoanisole Sulfate, 4-Amino-2-Hydroxytoluene, 4-Chlororesorcinol, m-Aminophenol, m-Phenylenediamine, m-Phenylenediamine Sulfate, 2-Nitro-p-Phenylenediamine, p-Aminophenol, p-Phenylenediamine, p-Phenylenediamine Sulfate, Resorcinol, and mixtures thereof.

7. The composition of claim 1, wherein the composition comprises 0.001% (w/w) to 5% (w/w) of the hair dye.

8. The composition of claim 1, wherein the composition comprises 0.01% (w/w) to 2.5% (w/w) of the hair dye.

9. The composition of claim 1, wherein the composition comprises 0.1% (w/w) to 1.5% (w/w) of the hair dye.

10. The composition of claim 1, wherein the solvent is selected from the group consisting of water, an alcohol, and mixtures thereof.

11. The composition of claim 1, wherein the solvent is selected from the group consisting of water, methanol, ethanol, propanol, isopropanol, butanol, sec-butanol, isobutanol, tert-butanol, 1-pentanol, 2-pentanol, 3-pentanol, 3-methyl-1-butanol, 2-methyl-1-butanol, 2,2-dimethyl-1-propanol, 3-methyl-2-butanol, 2-methyl-2-butanol, and mixtures thereof.

12. The composition of claim 1, wherein the solvent is selected from the group consisting of water, ethanol, and mixtures thereof.

13. The composition of claim 1, further comprising a co-solvent.

14. The composition of claim 1, further comprising a co-solvent selected from the group consisting of propylene glycol, glycerin, glycol ethers, and mixtures thereof.

15. The composition of claim 1, further comprising a co-solvent selected from the group consisting of 2-methoxyethanol, 2-ethoxyethanol, 2-propoxyethanol, 2-isopropoxyethanol, 2-butoxyethanol, 2-phenoxyethanol, 2-benzyloxyethanol, 2(2-methoxyethoxy)ethanol, 2(2-ethoxyethoxy)ethanol, and 2-(butoxyethoxy)ethanol.

16. A method for coloring hair, comprising contacting hair with a composition comprising:
    an N,N'-alkylurea selected from the group consisting of N,N'-dimethyl urea, N,N'-dimethylpropylene urea, N,N'-tetrabutyl urea and mixtures thereof,
    a hair dye, acrylic acid diallyldimethylammonium chloride polymer and
    a solvent.

17. A hair coloring composition produced by a process comprising mixing ingredients comprising:
    an N,N'-alkylurea selected from the group consisting of N,N'-dimethyl urea, N,N'-dimethylpropylene urea, N,N'-tetrabutyl urea and mixtures thereof,
    a hair dye, acrylic acid diallyldimethylammonium chloride polymer and
    a solvent.

* * * * *